United States Patent [19]
Maeno

[11] Patent Number: 5,194,815
[45] Date of Patent: Mar. 16, 1993

[54] DETECTING APPARATUS OF CONDUCTIVE MATERIAL CONTAINED IN STRINGY MATERIAL

[75] Inventor: Yorihiko Maeno, Tokyo, Japan
[73] Assignee: Dipole Electronics Co., Ltd., Tokyo, Japan
[21] Appl. No.: 768,913
[22] PCT Filed: Jan. 30, 1991
[86] PCT No.: PCT/JP91/00107
§ 371 Date: Sep. 27, 1991
§ 102(e) Date: Sep. 27, 1991
[87] PCT Pub. No.: WO91/11706
PCT Pub. Date: Aug. 8, 1991

[30] Foreign Application Priority Data

Feb. 5, 1990 [JP] Japan ............................. 2-25563

[51] Int. Cl.$^5$ ............................................. G01N 22/00
[52] U.S. Cl. ................................. 324/501; 324/632; 324/636; 324/558; 324/554; 340/552; 73/159; 73/160
[58] Field of Search ................... 250/227.11, 215; 340/552, 553; 324/536, 632, 636, 635, 501, 558, 554

[56] References Cited

U.S. PATENT DOCUMENTS

| | | | |
|---|---|---|---|
| 3,857,091 | 12/1974 | Kalifon | 324/536 |
| 4,507,605 | 3/1985 | Geisel | 324/501 |
| 4,580,132 | 4/1986 | Kato | 340/552 |
| 4,890,054 | 12/1989 | Maeno et al. | |

FOREIGN PATENT DOCUMENTS 57-165747 10/1982 Japan.
63-145951 6/1988 Japan.

Primary Examiner—Kenneth A. Wieder
Assistant Examiner—Jose M. Solis
Attorney, Agent, or Firm—Frishauf, Holtz, Goodman & Woodward

[57] ABSTRACT

A detector for detecting conductive materials contained in a stringy material sensitively, which is a cylindrical microwave cavity resonator (1) comprising a peripheral part (9) and two circular plates (10) covering the ends of the peripheral part. At least one of the circular plates has cylindrical protrusion (4) at its center. In the peripheral part, an antenna (5) for the generation of discharge is provided. In the protrusion (4) a detecting means (6) for discharge is provided. Paths (3,8) or a notched part (7) for the stringy material to be measured which passes through a high electric field formed by the protrusions and penetrate the cylindrical microwave cavity resonator oscillating at a fixed frequency, discharges are generated by the strong electric fields concentrated on the very small metals. Since sounds, light, and electromagnetic waves are generated at this time, the very small metals can be detected sensitively with discharge detecting means such as a microphone, a photodetector and an antenna.

10 Claims, 5 Drawing Sheets

DETECTING APPARATUS OF CONDUCTIVE MATERIAL CONTAINED IN STRINGY MATERIAL

TECHNICAL FIELD

The present invention relates to a detecting apparatus of conductive material such as metal contained in a stringy material such as glass fibers positioned in a cylindrical microwave cavity resonator.

BACKGROUND ART

With development of high density mounting technology, severer requirements such as high withstand voltage have been imposed on printed circuit boards on which electronic devices are mounted in a high density. These kind of printed circuit boards are formed by superposing a plurality of (e.g. seven) cloths, woven of glass fibers with paste, interposing epoxy resin between them.

If a high voltage is applied to printed circuit boards made of glass fibers containing minute metal pieces, discharges occur due to the minute metal pieces, so that it is impossible to get printed circuit boards with high withstand voltage if they use glass fibers containing minute metal pieces. Therefore it is necessary to use glass fibers without minute metal pieces for manufacturing high quality printed circuit boards. The development of technology to detect minute metal pieces contained in glass fibers has been a longstanding need in this technical field. The applicant of the present application already proposed in JP Pat. Kokai No. 63-145951 a microwave cavity resonator in which a protrusion is arranged in the center so that physical quantities of stringy materials can be precisely measured. As shown in FIGS. 5A and B, the cylindrical microwave cavity resonator 1 comprises protrusion 4 on its center and space 3 for passing stringy material 2 arranged on the center of protrusion 4 and the wall of the microwave cavity resonator opposed to the protrusion.

Such microwave cavity resonator 1 allows to measure metals contained in stringy materials such as glass fibers. To do so glass fibers without metal pieces are first placed at space 3 and then resonance characteristic for the glass fibers are measured with a measuring instrument of resonance characteristic by scanning the frequencies of microwave supplied to the microwave cavity resonator 1 from antenna 5, which frequencies are changed by changing the voltage of the voltage control oscillator. Next if glass fibers containing metal pieces are placed at space 3 for measuring resonance characteristics, the resonance characteristics will be different from that of the glass fibers without metal pieces. Measuring of shifted amount in resonant frequency and decreased amount in resonance peak voltage enables not only to detect metals contained but also to measure the accurate amount of contained metal.

The method of detecting metals by the change of resonance characteristics in this manner has an advantage to obtain accurate measurement results, but it has a disadvantage that the total system costs too much because it needs a voltage control oscillator and a measuring instrument of the resonance characteristics. In case of glass fibers by which printed circuit boards for high density assembling are manufactured, measuring the amount of contained metals is not necessary but only detection of contained metals is necessary. Furthermore in factories hundreds of, glass fibers are manufactured at the same time and a detecting apparatus for contained metals is needed for every glass fiber, so that the total cost of the detecting apparatus would be enormous. Therefore an acceptable detecting apparatus of contained metals in a stringy material must be inexpensive. In this sense the measuring apparatus for physical quantities disclosed in Pat. Kokai No. 63-145951 has some disadvantage when the introduction of the apparatus to factories of manufacturing glass fibers is considered.

On the other hand, in case of glass fibers used for high density printed circuit boards the only problem is whether or not metals are contained in the glass fibers. From this point of view, the detecting apparatus of physical quantities, as disclosed in Pat. Kokai No. 63-145951, which can measure not only the existence of metals but also accurately measure the amount of contained metals is an unnecessarily accurate detecting apparatus for use when manufacturing glass fibers.

One of objects of the present invention is to provide an inexpensive detecting apparatus of conductive materials which can accurately detect the existence of minute metal pieces contained the material to be measured such as stringy materials.

The present invention solves the above mentioned problem by providing a detecting apparatus of conductive materials contained in a stringy material comprising a cylindrical microwave cavity resonator having a circumferential portion and disks covering the both ends of the circumferential portion, which comprises a cylindrical protrusion arranged on the center of at least one of the disks, at least one antenna provided on the circumferential portion, a detecting means for discharge, and a pass for the stringy material to be measured arranged in high electric field region formed by the protrusion and penetrating the cylindrical microwave cavity resonator.

When detecting of conductive materials such as minute metal pieces contained in stringy materials with the detecting apparatus of conductive materials of the invention, the microwave cavity resonator is made to resonate at a constant frequency by microwaves supplied from a discharge generating antenna. The microwave cavity resonator of the detecting apparatus of the invention comprises at least one protrusion at its center where the electric field is enhanced. The pass for the stringy materials to be measured penetrating the cylindrical microwave cavity resonator is arranged at a place where the the electric field is the highest. If minute metal pieces contained in the stringy materials locate at such place, the electric fields concentrate to the minute metal pieces, so that discharge will occur. At this time, since lights, sound and electromagnetic waves are generated, discharges can be detected by a discharge detecting means such as a photodiode, a microphone, or a loop antenna. In this way metal pieces contained in the stringy materials can be sharply detected.

The only required function for the microwave generator used in the apparatus of the invention is to generate a discharge, so that it does not need an expensive voltage control oscillator which is essential for the prior method for measuring shift in resonance characteristic. Inexpensive magnetrons which are commonly used in consumer electric ranges are suitable enough for generators used in the system of the invention. In addition expensive measuring circuit for resonance characteristic, which is necessary for the prior measuring method, is not needed. Therefore the detecting apparatus of the invention is a very inexpensive apparatus which can be employed in a large quantity in factories of manufacturing glass fibers.

The apparatus characterized in that the two protrusions are opposed each other can supply larger electric fields to the stringy materials to be measured than the apparatus with only one protrusion.

In case of the apparatus characterized in that the pass is a vertical notch extending from the center axis to the circumferential portion, it is easy to set stringy materials to be measured on said apparatus because a user only need to move the stringy material to be measured from its circumferential portion to the center. In addition very few microwaves leak from said apparatus at the time of measurement, so that it is not necessary to cover the notch portion with dielectric after setting the stringy materials to be measured on the pass.

The apparatus characterized in that the pass is a vertical notch extending from the center axis to the circumferential portion has an advantage that setting stringy materials to be measured on said apparatus is easy. The apparatus characterized in that the pass is a penetrated hole including the center axis of the microwave cavity resonator and the apparatus characterized in that apertures are arranged on the circumferential portion where a straight line perpendicular to the center axis of the microwave cavity resonator hits, have both an advantage that microwaves leaked from the microwave cavity resonator at the time of measurement are fewer than ones in the apparatus without said notch.

DETAILED DESCRIPTION OF THE INVENTION

Figure 1A:
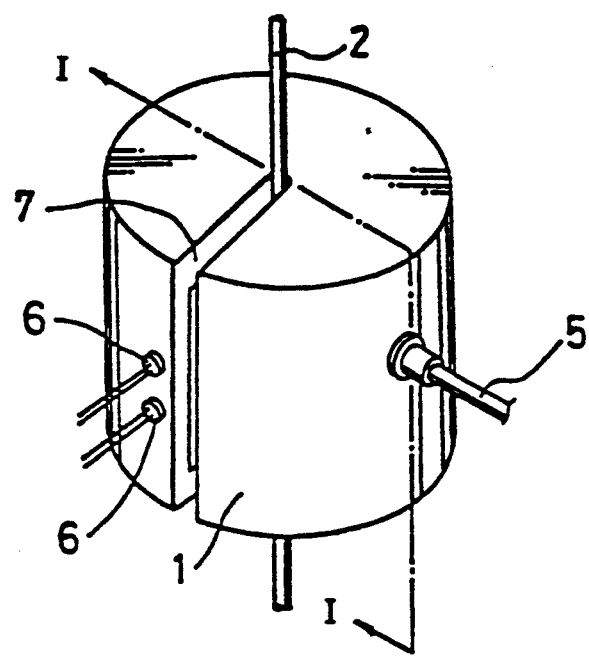
FIG. 1A shows the microwave cavity resonator of the invention in which a notch portion is arranged vertically.

The detecting apparatus of conductive material of the invention will be explained further with attached figures.

EXAMPLE 1

The first example of a detecting apparatus of conductive material of the present invention will be explained with FIGS. 1A and B.

The apparatus of the example comprises a cylindrical microwave cavity resonator 1 (inside diameter: 50 mm, outside diameter: 70 mm) at the center of which opposing cylindrical protrusions 4 with a diameter of 22 mm are arranged. The distance in the axial direction between internal walls of two disks 10 of the microwave cavity resonator 1 is 45 mm and the height of the protrusion 4 is 14 mm, so that separation between both protrusions 4 is 17 mm.

The microwave cavity resonator 1 is provided with notch portion 7 with a width of 4 mm and extending from the center of protrusion 4 to the circumferential portion 9 of the resonator. A user can easily set the stringy material on the center of the apparatus through such notch portion 7. FIG. 1B shows a sectional view along a broken line I—I in FIG. 1A on which the stringy material 2 is set.

Figure 1B:
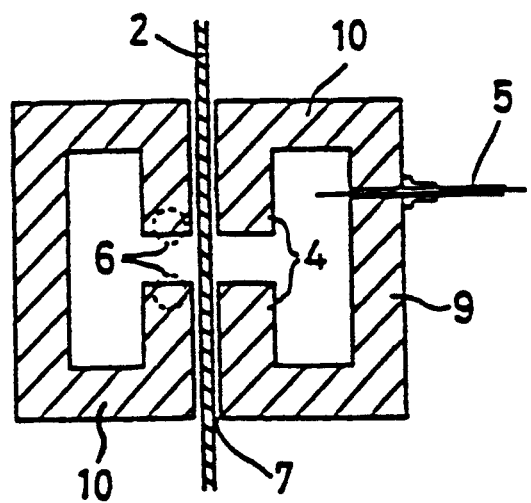
FIG. 1B is a sectional view along line I—I in FIG. 1A.

As shown in FIG. 1A, the circumferential portion 9 of microwave cavity resonator 1 is provided with two photodiodes 6 near the notch portion 7 and a straight antenna 5. The antenna 5 is connected to a magnetron having an output of 10 W and a frequency of 2.45 GHz. The photodiodes 6 are arranged on a location such that light generated by discharges due to minute metal pieces contained in stringy material 2 can be detected.

For detecting metals contained in the stringy material 2 with this apparatus as shown in FIG. 1A, the stringy material should be placed at the place where the electric field is the largest, that is to say, at the center of the microwave cavity resonator 1. Next, microwaves with a frequency of 2.45 GHz and an output of 1 W is supplied into the microwave cavity resonator 1 through the antenna 5 so as to resonate. If there are minute metal pieces in the stringy material 2 under said condition, discharges with sounds and lights will be generated. The discharge is detected with the two photodiodes 6 arranged in different places. Stainless steel balls with a diameter of 0.2 mm and copper metal pieces with a length of 5 mm and a diameter of 10 micron meter contained in glass fibers could be detected with this apparatus.

In case of the apparatus of example 1, microwaves leaked from the notch portion 7 can be neglected under said resonance condition. Therefore there is no need to cover the notch portion 7 with conductor in order to prevent the leakage of microwave which is dangerous to a human body.

EXAMPLE 2

Figure 2A:
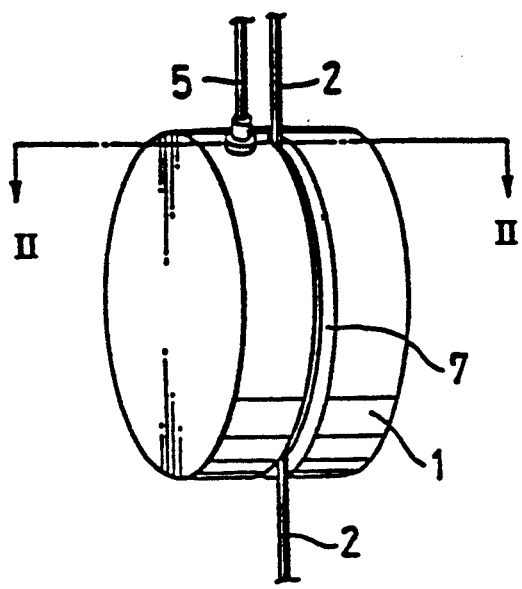
FIG. 2A shows the microwave cavity resonator of the invention in which a notch portion is arranged horizontally.
Figure 2B:
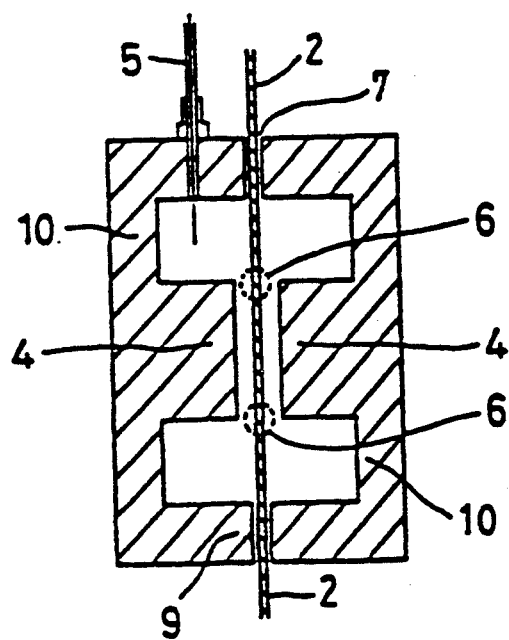
FIG. 2B is a sectional view along line II—II in FIG. 2A.

The second example of the apparatus of the invention will be explained with FIGS. 2A and B.

The apparatus in this example is provided with the notch portion 7 in the transverse direction. The two photodiodes 6 are arranged on the part of circumferential portion 9 facing on the notch portion 7.

Unlike the apparatus of example 1, microwaves leaked from the notch portion can not be neglected in this example. Therefore in order to prevent danger to human bodies the notch portion 7 should be covered with conductor after the stringy material being set on a desired position. The conductor is not necessarily a metal plate. A metal foil can also prevent the leakage of microwaves to the outside of the apparatus.

EXAMPLE 3

Figure 3A:
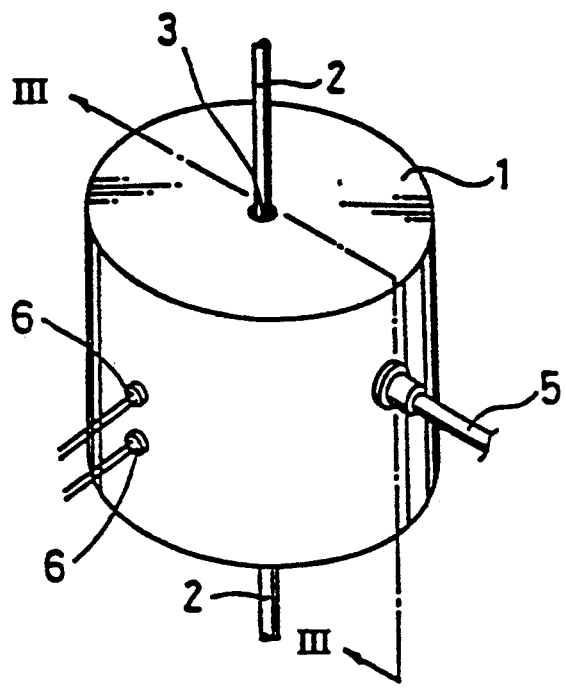
FIG. 3A shows the microwave cavity resonator of the invention in which a penetrating hole is arranged vertically.
Figure 3B:
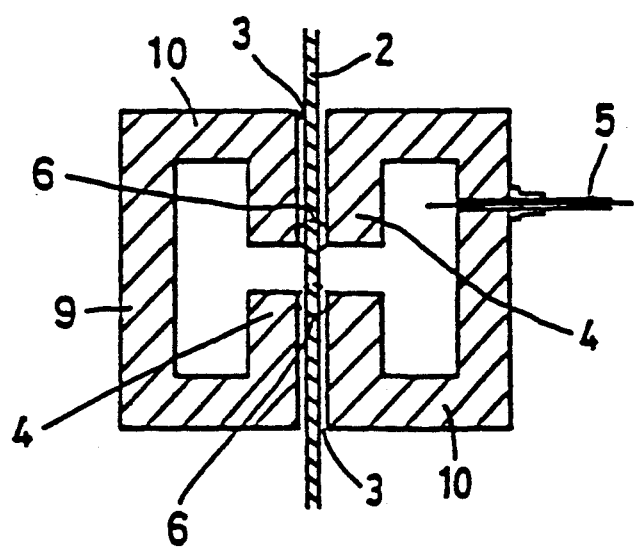
FIG. 3B is a sectional view along line III—III in FIG. 3A.

The third example of the apparatus of the invention will be explained with FIGS. 3A and B.

The apparatus in this example comprises penetrating hole 3 having a diameter of 4 mm arranged at the center axis of the protrusion 4 enabling the stringy material pass through.

Unlike the apparatus in examples 1 and 2, the apparatus in this example is not provided with the notch portion, so that microwaves do not leak, which results in the improvement of measurement accuracy.

EXAMPLE 4

Figure 4A:
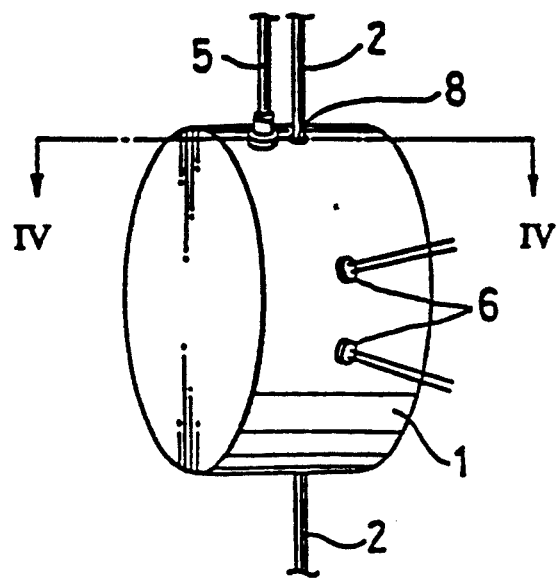
FIG. 4A shows the microwave cavity resonator of the invention in which apertures for the stringy material to be measured are arranged on the circumferential wall.
Figure 4B:
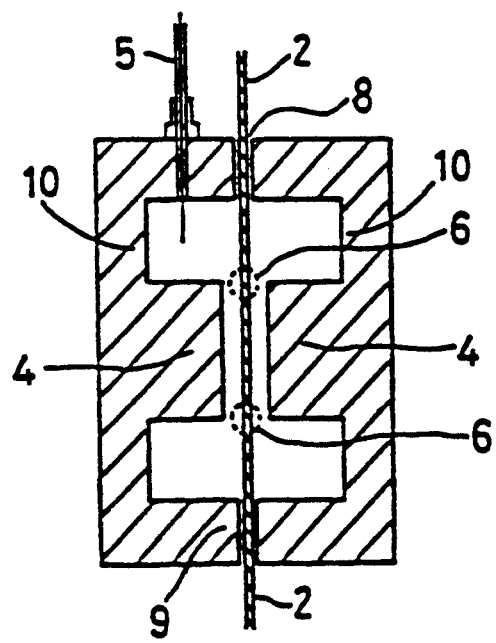
FIG. 4B is a sectional view along line IV—IV in FIG. 4A.
Figure 5A:
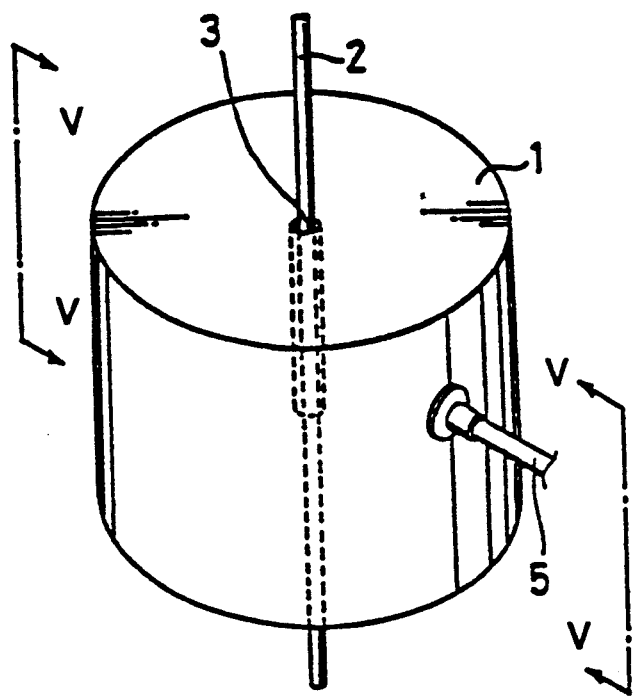
FIG. 5A shows the microwave cavity resonator of the prior art.
Figure 5B:
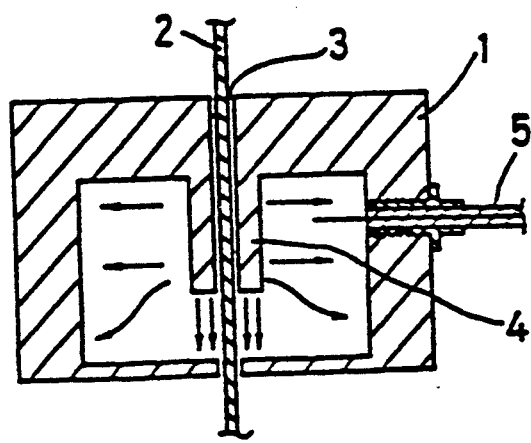
FIG. 5B is a sectional view along line V—V of the microwave cavity resonator in FIG. 5A.

The fourth example of the apparatus of the invention will be explained with FIGS. 4A and B.

The apparatus in this example comprises penetrating holes 3 having a diameter of 4 mm at both ends of the circumferential portion in such a way that the stringy materials pass through the center of the protrusion and a space formed by the two separated protrusions.

The apparatus has the same effect as one of example 3, and furthermore does not have disadvantage in example 3 that undesired discharges easily occur between the protrusions.

In the examples explained above, discharge states caused by minute metal pieces contained in the stringy material is detected by lights. However the discharge states can be detected with sounds collected by a microphone instead of lights. Furthermore discharge detection with eletromagnetic waves by means of a loop antenna and a detector is possible. In this case, the frequency of the generated electromagnetic waves is different from the resonant frequency $f_3$. Therefore if the loop antenna and the detector are designed so as to detect frequency $f_3$, electromagnetic waves allow to detect minute metal pieces.

Furthermore those microwave cavity resonators described hereinbefore have two protrusions, but it is allowable that the resonator has only one protrusion so that the protrusion faces a flat wall.

INDUSTRAL APPLICABILITY

As explained above, the detecting apparatus for conductive materials of the invention is suitable to detecting conductive materials such as minute metal pieces contained in the stringy materials such as glass fibers.

I claim:

1. A detecting apparatus for detecting conductive materials contained in a stringy material, comprising:
    a cylindrical microwave cavity resonator having a vertical center axis, said microwave cavity resonator including:
       at least one antenna for generating microwaves, positioned on a circumferential portion of said microwave cavity resonator;
       first and second disks for respectively covering first and second end portions of said circumferential portion of said microwave cavity resonator, at least one of said first and second disks having a cylindrical protrusion on a center portion thereof; and
       discharge detecting means for detecting a discharge in said microwave cavity resonator induced by a conductive material contained in the stringy material received in said microwave cavity resonator, when said at least one antenna generates microwaves in said microwave cavity resonator;
    a vertical notch formed in said microwave cavity resonator, said vertical notch extending from said vertical center axis of said microwave cavity resonator to said circumferential portion of said microwave cavity resonator, said stringy material being insertable into said vertical notch from said circumferential portion of said microwave cavity resonator and being directed by said vertical notch into a central area of the microwave cavity resonator where a high electric field is generated by said protrusion on said at least one of said first and second disks when said antenna generates said microwaves.

2. An apparatus as claimed in claim 1, wherein said discharge detecting means comprises a photodiode.

3. An apparatus as claimed in claim 1, wherein the discharge detecting means comprises a microphone.

4. An apparatus as claimed in claim 1, wherein the discharge detecting means comprises a loop antenna.

5. An apparatus as claimed in claim 1, wherein both of said first and second disks respectively have a protrusion provided thereon, said protrusions of said first and second disks being positioned in said microwave cavity resonator to oppose each other.

6. A detecting apparatus for detecting a conductive material contained in a stringy material, comprising:
    a cylindrical microwave cavity resonator having a vertical center axis, said microwave cavity resonator including:
       at least one antenna for generating microwaves, positioned on a circumferential portion of said microwave cavity resonator;
       first and second disks for respectively covering first and second end portions of said circumferential portion of said microwave cavity resonator, at least one of said first and second disks having a cylindrical protrusion on a center portion thereof; and
       discharge detecting means for detecting a discharge in said microwave cavity resonator induced by a conductive material contained in the stringy material received in said microwave cavity resonator, when said at least one antenna generates microwaves in said microwave cavity resonator;
    a semicircular notch provided in said microwave cavity resonator, said semicircular notch being formed in a transverse plane that is perpendicular to said center axis of said microwave cavity resonator, said semicircular notch extending from said center axis of said microwave cavity resonator to said circumferential portion of said microwave resonator, said stringy material being insertable into said semicircular notch at said circumferential portion of said microwave cavity resonator and being directed by said semicircular notch into a central area of the microwave cavity resonator where a high electric field is generated by said protrusion on said at least one of said first and second disks, when said antenna generates said microwaves.

7. An apparatus as claimed in claim 6, wherein said discharge detecting means comprises a photodiode.

8. An apparatus as claimed in claim 6, wherein said discharge detecting means comprises a microphone.

9. An apparatus as claimed in claim 6, wherein said discharge detecting means comprises a loop antenna.

10. An apparatus as claimed in claim 6, wherein said first and second disks respectively have a protrusion provided thereon, said protrusions of said first and second disks being positioned in said microwave cavity resonator to oppose each other.

* * * * *